US008055050B2

(12) United States Patent
Roessl et al.

(10) Patent No.: US 8,055,050 B2
(45) Date of Patent: Nov. 8, 2011

(54) MOTION COMPENSATION IN ENERGY-SENSITIVE COMPUTED TOMOGRAPHY

(75) Inventors: Ewald Roessl, Hamburg (DE); Udo Van Stevendaal, Ahrensburg (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 517 days.

(21) Appl. No.: 12/377,297

(22) PCT Filed: Jul. 23, 2007

(86) PCT No.: PCT/US2007/074103
§ 371 (c)(1),
(2), (4) Date: Feb. 12, 2009

(87) PCT Pub. No.: WO2008/021664
PCT Pub. Date: Feb. 21, 2008

(65) Prior Publication Data
US 2010/0208962 A1   Aug. 19, 2010

Related U.S. Application Data

(60) Provisional application No. 60/822,393, filed on Aug. 15, 2006.

(51) Int. Cl.
*G06K 9/00* (2006.01)
*A61B 6/03* (2006.01)
(52) U.S. Cl. ............................. 382/131; 378/5
(58) Field of Classification Search .................. 382/131; 378/5, 57, 62
See application file for complete search history.

(56) References Cited

U.S. PATENT DOCUMENTS

| 5,383,231 | A | 1/1995 | Yamagishi |
| 5,602,891 | A * | 2/1997 | Pearlman ........................ 378/62 |
| 6,426,990 | B1 | 7/2002 | Cesmeli |
| 7,894,568 | B2 * | 2/2011 | Ziegler ............................ 378/57 |
| 2005/0018808 | A1 | 1/2005 | Piacsek et al. |

FOREIGN PATENT DOCUMENTS

| WO | 9717673 A1 | 5/1997 |
| WO | 2005009206 A2 | 2/2005 |

OTHER PUBLICATIONS

Woodhouse, et al., Coronary Arteries: Retrospective Cardiac Gating Technique to Reduce Cardiac Motion Artifact at Spiral CT, Radiology, Aug. 1997, pp. 566-569, vol. 204, No. 2.
Meijering, E. H. W., et al.; Retrospective Motion Correction in Digital Subtraction Angiography: A Review; 1999; IEEE Trans. on Medical Imaging; 18(1)20 pages.
Grangeat, et al., Dynamic X-ray Computed Tomography, LETI CEA Annual Review 2002, Jun. 25, 2002, pp. 1-19 Dyn/02E-210/.
Llopart et al., Medipix2: a 64-k Pixel Readout Chip With 55-μm Square Elements Working in Single Photon Counting Mode, IEEE Transactions on Nuclear Science, Oct. 2002, pp. 2279-2283, vol. 49, No. 5.

(Continued)

*Primary Examiner* — Seung C Sohn

(57) ABSTRACT

An imaging system includes an energy resolving detector (20) which generates data indicative of detected radiation having at least first and second energies. The system also includes an energy pre-processor (24), a motion calculator (26), and a reconstructor (22). In one embodiment, the apparatus uses a k-edge imaging technique to perform a motion compensated reconstruction of projection data indicative of an object under examination.

26 Claims, 3 Drawing Sheets

OTHER PUBLICATIONS

Llopart et al., First test measurements of a 64k pixel readout chip working in single photon counting mode, Nuclear Instruments and Methods in Physics Research A, 2003, pp. 157-163, 509.

Blondel, C., et al.; 3D tomographic reconstruction of coronary arteries using a precomputed 4D motion field; 2004; Phys. Med. Biol.; 49:2197-2208.

* cited by examiner

MOTION COMPENSATION IN ENERGY-SENSITIVE COMPUTED TOMOGRAPHY

CROSS REFERENCE TO RELATED APPLICATIONS

This application claims the benefit of U.S. provisional application Ser. No. 60/822,393 filed Aug. 15, 2006, which is incorporated herein by reference.

The present application relates to motion compensation in computed tomography (CT). While it finds particular application to cardiac imaging in medicine, it also relates to other medical and non-medical applications in which it is desirable to compensate for motion in an object under examination.

CT scanners have proven to be invaluable in medical and other applications in which it is necessary to obtain information about the internal structure or function of an object. In medical imaging, for example, CT scanners are widely used to provide images of and other information regarding the physiology of human patients. A relatively recent trend has been the adoption of multi-slice CT, as increasing the axial coverage of a CT scanner can have a number of advantages, including an improved ability to scan moving portions of the anatomy, shorter scan times, and improved scanner throughput.

One important application of computed tomography is cardiac imaging. Although the increased axial coverage of multi-slice scanners, the use of relatively faster gantry rotation speeds, and other advances have improved the temporal resolution of practical CT systems, the motion of the beating heart can lead to blurring and other artifacts in the reconstructed image data.

One technique for reducing the impact of cardiac and other motion has been the use of gating techniques. In prospective cardiac gating, for example, the scan is conducted so that projection data is acquired at the desired phase or phases of the cardiac cycle. In retrospective cardiac gating, projection data acquired during the course of a scan is selected or gated for reconstruction based on the cardiac phase at which it was acquired. The projection data is selected so as to obtain projection data collected over an angular range which provides a complete CT data set. See, e.g., Woodhouse et al., *Coronary Arteries: Retrospective Cardiac Gating Technique to Reduce Cardiac Motion Artifact in Spiral CT*; Radiology 1997:566-569.

While these techniques have proven useful, there remains room for improvement. More particularly, it remains desirable to provide an improved motion compensated reconstruction of an object of interest.

Aspects of the present application address these matters and others.

In accordance with one aspect, a computed tomography apparatus includes a motion calculator and a reconstructor. The reconstructor reconstructs energy resolved first radiation projection data to generate first image data indicative of an object under examination at at least first and second motion states. The motion calculator uses the first image data to calculate a motion of the object, and the reconstructor further performs a motion compensated reconstruction using the calculated motion and second radiation projection data to generate second image data indicative of the object.

According to another aspect of the invention, a tomographic method includes reconstructing energy resolved first projection data to generate first image data indicative of an object at at least first and second motion states, using the first image data to estimate a motion of the object, and reconstructing second projection data to generate second image data indicative of the object. Reconstructing the second projection data includes using the estimated motion to compensate for a motion of the object during acquisition of the second projection data.

According to another aspect, a computer readable storage medium containing instructions which, when executed by a computer, cause the computer to carry out a method which includes, performing an energy processing operation to identify a substance of interest in an object, estimating a motion of the identified substance, and using the estimated motion to perform a motion compensated reconstruction of tomographic projection data indicative of the object.

According to another aspect, an apparatus includes an object support adapted to support a subject in an examination region, an x-ray source which rotates about the examination region, an x-ray detector which acquires energy resolved projection data, and means for using the energy resolved projection data to perform a motion compensated reconstruction of projection data acquired by the detector. The projection data includes first data indicative of detected x-rays having a first energy and second data indicative of detected x-rays having a second energy;

Still further aspects of the present invention will be appreciated to those of ordinary skill in the art upon reading and understand the following detailed description.

The invention may take form in various components and arrangements of components, and in various steps and arrangements of steps. The drawings are only for purposes of illustrating the preferred embodiments and are not to be construed as limiting the invention.

Figure 1:
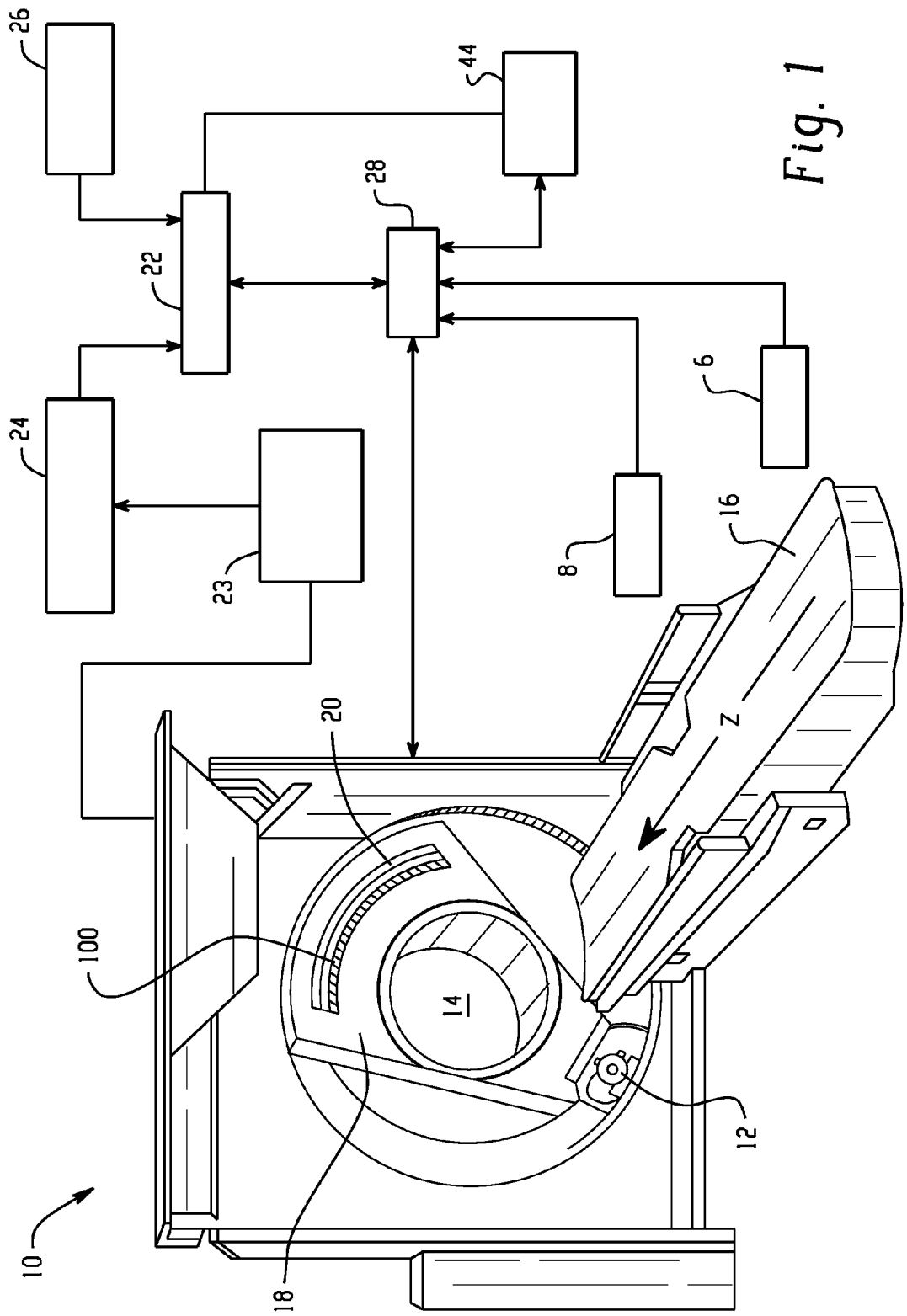
FIG. 1 depicts a computed tomography system.

With reference to FIG. 1, a CT scanner 10 includes a rotating gantry 18 which rotates about the z-axis. The gantry 18 supports a polychromatic x-ray source 12 such as a conventional x-ray tube and an energy resolving x-ray detector 20 which generates x-ray projection data at a plurality of projection angles or views with respect to the examination region 14.

The detector 20 includes a generally two dimensional array of detector elements 100 which generate outputs indicative of detected radiation falling within a plurality of energy ranges or bins $b_i$. Energy resolving detectors may be implemented using photon counting detectors, for example as disclosed in Llopart, X., et al., *First test measurements of a 64k pixel readout chip working in a single photon counting mode*, Nucl. Inst. and Meth. A, 509(1-3): 157-163 (2003); Llopart, X., et al. *Medipix2:A 64-k pixel readout chip with 55 μm square elements working in a single photon counting mode*, IEEE Trans. Nucl. Sci. 49(5):2279-2283 (2002). Other energy resolving detector implementations using multiple scintillators, direct conversion or other detectors, energy filters, other photon counting detector implementations, or other suitable energy resolving techniques either alone or in combination are also contemplated.

An object support 16 such as a couch supports a patient or other subject in the examination region 14. The object support 16 is advantageously movable in coordination with a scan so as to provide a circular, helical, saddle, or other desired scan trajectory. A contrast agent injector 6 operatively connected to the controller 28 provides for the injection of an iodinated or other contrast agent, and a biological monitor 8 such as an electrocardiogram (ECG) monitor provides information regarding the cardiac phase or other motion state of the subject. As is conventional in the art, the biological monitor 8 signal can in the case of retrospective gating be used to correlate the projection data with the motion phase or state at which it was acquired. In prospective gating, the biological monitor signal 8 can be used to acquire data at the desired motion state(s) or phase(s).

An energy pre-processor 24 processes the information from the energy resolving detector 20 to generate projection data indicative of an energy or material of particular interest. In one implementation, and as will be discussed further below, the energy pre-processor 24 processes the detector 20 signals to generate projection data representative of a contrast agent injected using the injector 6 or otherwise present in the subject.

A reconstructor 22 reconstructs projection data from the energy pre-processor 24 to generate image data. In the case of a retrospectively gated reconstruction, projection data corresponding to one or more desired motion states or phases of the subject or a region of interest thereof is used to reconstruct image data corresponding to the desired phase(s). In one implementation, and as will be discussed further below, the reconstructor 22 operates on projection data which has been processed by the energy pre-processor 26 to generate image data which is indicative largely of the contrast agent or other material of interest at each of a plurality of motion states or phases. A motion calculator 26 uses the reconstructed image data to estimate a motion of the object. The motion information is then used by the reconstructor 22 to carry out a motion compensated reconstruction.

A general purpose computer serves an operator console 44. The console 44 includes a human readable output device such as a monitor or display and an input device such as a keyboard and mouse. Software resident on the console allows the operator to control the operation of the scanner 10 by establishing desired scan protocols, initiate and terminate scans, view and otherwise manipulate images and other data from the scans, and otherwise interact with the scanner 10, for example through a graphical user interface (GUI).

Figure 2:
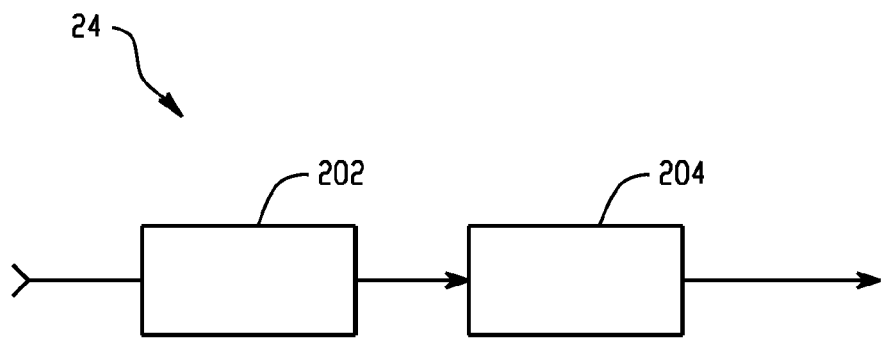
FIG. 2 depicts an energy pre-processor.

As noted above, the energy pre-processor 24 processes the projection data from the detector 20 to provide projection data having a desired spectral characteristic. In one implementation, and with reference to FIG. 2, the pre-processor 24 employs a k-edge imaging technique to generate projection data indicative of a contrast agent or other substance present in the subject.

The inputs to the energy pre-processor 24 include energy resolved detector signals $d_1, d_2 \ldots d_i$ indicative of energy detected in a plurality of energy ranges or bins. In the case of k-edge detection, i is preferably greater than or equal to three (3). The detection signals $d_i$ exhibit a spectral sensitivity $D_i(E)$ of the i-th energy bin or range $b_i$. Furthermore, the emission spectrum $T(E)$ of the polychromatic radiation source 12 is generally known.

A modeling unit 202 models the attenuation by the subject as a combination of the photo-electric effect with characteristic attenuation spectrum $P(E)$, the Compton effect with characteristic attenuation spectrum $C(E)$, and the substance (e.g., a contrast medium) with a k-edge in an energy range of interest and a characteristic attenuation spectrum $K(E)$. The density length product for each of the components, in particular that of the photo-effect component p, the Compton effect component c, and the k-edge component k, enter the modeling of each detection signal $d_i$ according to the relationship:

$$d_i = \int dE \cdot T(E) \cdot D_i(E) \cdot \exp(-p \cdot P(E) - c \cdot C(E) - k \cdot K(E))  \quad \text{Equation 1}$$

Where at least three detection signals $d_1, d_2, d_3$ are available for at least three energy ranges or bins $b_1, b_2, b_3$, a system of at least three equations is formed having three unknowns, which can thus be solved with known numerical methods in a calculation unit 204. It is preferred to use a maximum likelihood approach that takes the noise statistics into account. The results, in particular the components p, c, and k, can then be used alone or in combination to reconstruct images of the desired component using conventional reconstruction methods.

While three energy ranges or bins $b_i$ are generally sufficient to determine the components p, c, and k, improved sensitivity and noise robustness may generally be obtained by improving the energy resolution of the input signal, for example by increasing the number of ranges or bins $b_i$.

The above energy processing technique is also disclosed in commonly assigned European Patent Application No. EP05108745.0, filed Sep. 22, 2005 and entitled CT Imaging System, which application is expressly incorporated by reference in its entirety herein.

As noted above, the motion calculator 26 uses reconstructed image data to calculate a motion of the object. An exemplary calculation will be described with reference to FIG. 3, which is a schematic representation of a reconstructed image space showing the location of two arbitrary points 302, 304.

Figure 3:
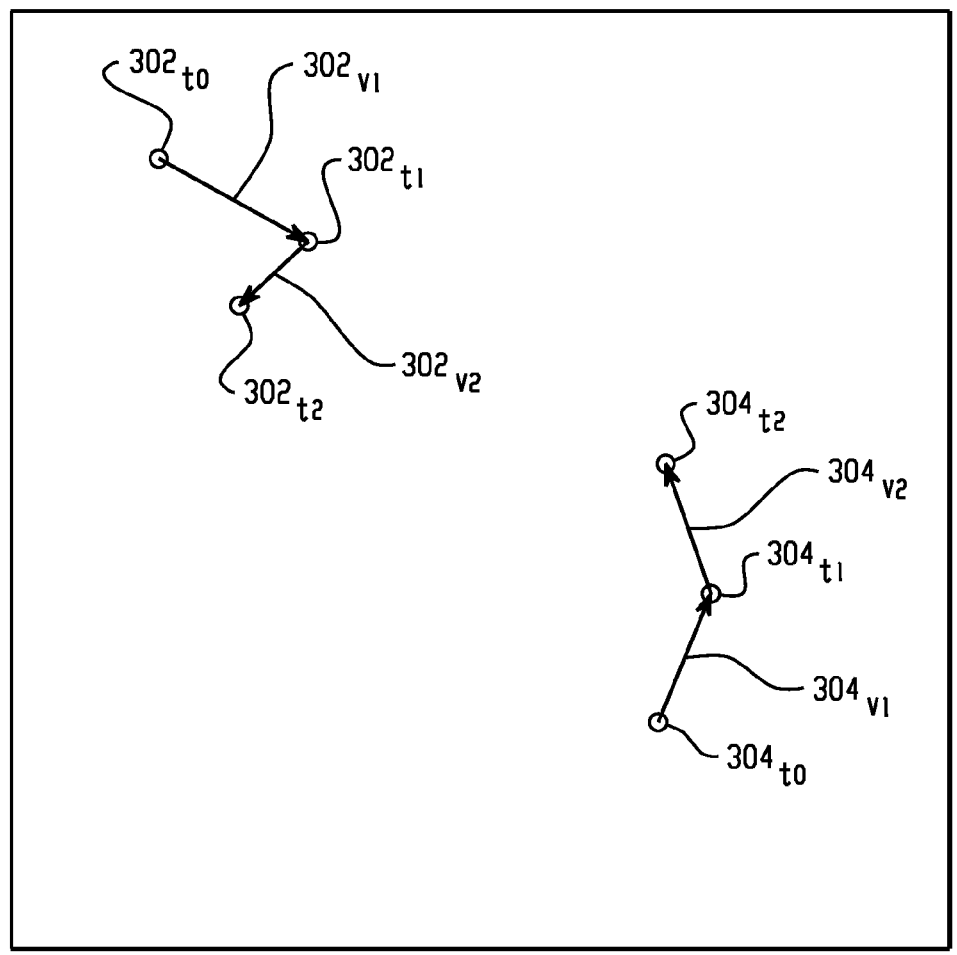
FIG. 3 depicts motion vectors indicative of the motion of an object.

The positions of point 302 at the respective measurement times or phases t0, t1, t2 is shown as $302_{t0}, 302_{t1}, 302_{t2}$; the position of point 304 is likewise depicted as $304_{t0}, 304_{t1}, 304_{t2}$. The motion calculator 26 uses the locations to calculate motion vectors $302_{V1}(x,y,z), 302_{V2}(x,y,z), 304_{V1}(x,y,z), 304_{V2}(x,y,z)$ which describe the motion of the points 302, 304 between the respective measurement times. While FIG. 3 depicts the motion in two (2) dimensions for ease of illustration, those of ordinary skill in the art will appreciate that, in the case of a three dimensional image volume, the motion vector would ordinarily be a three (3) dimensional vector. Note that the motion values may also be calculated for only one (1) or for three (3) or more points or regions. The motion vectors can also be calculated on other than a point-wise basis, for example by using shape fitting, elastic deformation, or other techniques to estimate a change in shape of the object or an ROI thereof. Additionally, the motion vector field can be determined for the entire volume by a spatial extra-/interpolation of the motion vectors at the different volume positions. The interpolation may be performed according to known techniques, for example using a simple linear interpolation, a thin plate spline interpolation, or the like. The order of the interpolation is typically a function of the number of acquired spatial locations. Similarly, the motion vectors may be calculated for only two (2) or for four (4) or more time periods or phase points.

Once the motion vector field has been determined for the entire volume or a sub-volume of interest and for a motion state of one cardiac phase to the motion state of another cardiac phase, the reconstructor 22 uses the motion vectors to perform a motion compensated reconstruction. In one such technique, the motion vectors are used directly in the motion compensation by modifying a voxel position in the reconstruction volume according to the cardiac phase of the projection to be backprojected. In other words, the motion compensated reconstruction should be performed for all projections within the temporal window around the cardiac phase from which the data are taken for a conventional gated CT reconstruction and based on that a determination of the motion vector field. The motion compensation may also be performed following at least one of a temporal or spatial interpolation of the motion vectors.

The calculation of the motion vectors (using segmented data) and a corresponding motion compensated reconstruction is also discussed in commonly assigned European Patent Application No. EP05111216.7, filed Nov. 24, 2005 and entitled Motion compensated CT reconstruction of high contrast objects, which application is expressly incorporated by reference in its entirety herein.

Figure 4:
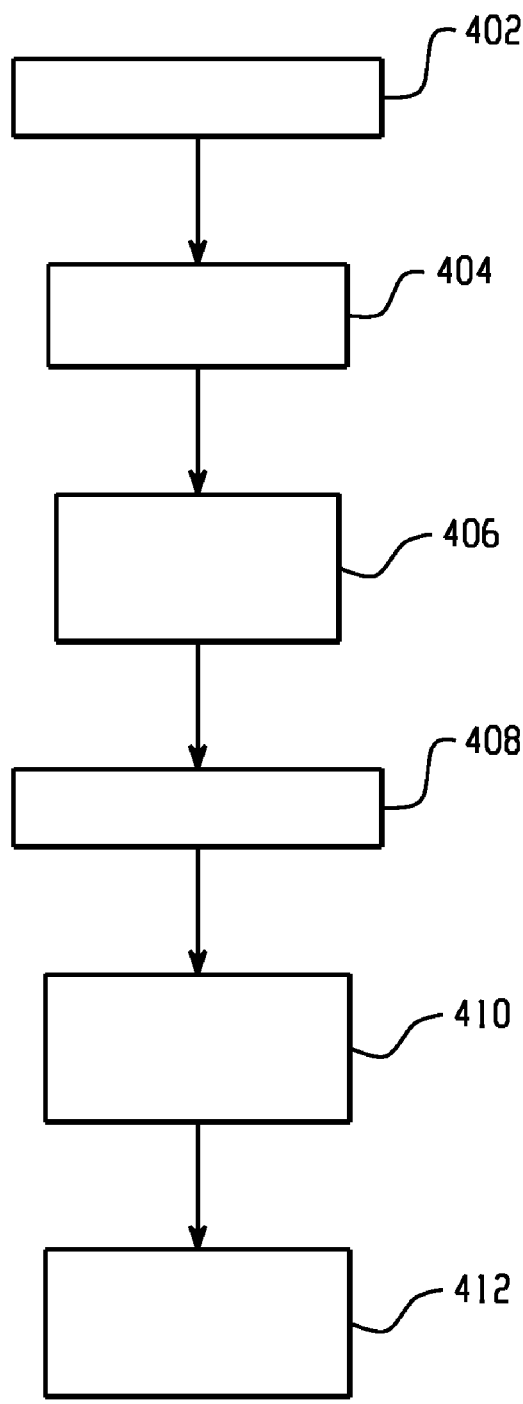
FIG. 4 depicts an imaging method.

With reference to FIG. 4, operation will now be described in relation to an exemplary contrast enhanced cardiac scan.

Scan data is acquired at 402, for example using a conventional low pitch helical, circular, saddle, or other desired scan trajectory. In the exemplary case of a contrast enhanced cardiac examination, a contrast agent is introduced into the anatomy of the subject in coordination with the scan using known techniques. Signals from the ECG 8 are also acquired in conjunction with the projection data.

An energy pre-processing is performed at 404. In the exemplary contrast enhanced cardiac scan, a k-edge processing technique is used to generate projection data indicative of contrast agent present in an ROI which includes at least a portion of the heart.

The pre-processed projection signals are reconstructed at step 406 to generate image data at each of a plurality of cardiac phases. It will be appreciated that, in the present k-edge imaging example, the reconstructed image data is largely indicative of the concentration of contrast agent in the region of the heart. As will also be appreciated, the contrast agent can ordinarily be expected to have a relatively greater contrast relative to the surrounding tissues as compared to images generated from a conventional polyenergetic CT data set.

The motion of the desired points or regions of the heart at one or more phase points is calculated at step 408. Note that, prior to performing the motion calculation, segmentation, clustering, or other suitable image processing operations may optionally be performed to further identify regions containing contrast agent.

At step 410, information from the motion calculations are used to perform a motion compensated reconstruction at one or more desired cardiac phases. In this regard, it should be noted that the motion compensated reconstruction may be performed on the k-edge data, photoelectric spectrum data, the Compton spectrum data (or a combination thereof), data processed to approximate a conventional polyenergetic data set, or other desired spectral data, whether pre-processed or otherwise.

At step 412, the reconstructed image data is displayed in human readable form, for example on a monitor associated with the operator console 44.

Variations are contemplated. For example, the spectral information may be obtained other than through the use of energy resolving detectors. Thus, for example, x-ray source(s) which produce radiation having the desired spectral characteristics and/or time varying or other filters which selectively harden or otherwise alter the spectral characteristics of the radiation may also be used.

Other pre-processing techniques which identify a substance of interest or otherwise provide a desired material separation may also be implemented. For example, basis material combinations other than photo/Compton, including but not limited to bone/soft tissue and calcium/water may also be provided. Depending on the technique, data indicative of two (2) energy ranges or bins may be used, for example where it is desirable to solve for the photoelectric and Compton components of the acquired projection data, or where it is desired to interpolate the energy resolved data. The energy pre-processor 24 may also be omitted, in which case the reconstructor 22 may operate directly on the energy resolved projection data. An energy-based post processor which operates on the image data may also be used to identify a substance of interest or otherwise provide a desired material separation.

While the above description has focused on cardiac imaging, the described techniques may also be used in connection with regions of interest other than the heart, or to compensate for respiratory or other motion.

The energy pre-processor 24, reconstructor 22, and motion calculator 26 may be implemented by way of computer readable instructions which, when executed by a computer processor(s), cause the processor(s) to carry out the described techniques. In such a case, the instructions are stored in a computer readable storage medium associated with or otherwise accessible to the relevant computer. Note also that the described techniques need not be performed concurrently with the data acquisition. They may also be performed using a computer (or computers) which are associated with the scanner 10; they may also be located remotely from the scanner 10 and access the relevant data over a suitable communications network such as a HIS/RIS system, PACS system, the internet, or the like.

It should also be noted that the reconstruction has been discussed in terms of a single reconstructor 22. The reconstructor 22 may include multiple reconstruction units or algorithms, for example a first reconstruction unit or algorithm which carries out a reconstruction used to calculate the object motion and a second unit or algorithm which carries out the motion compensated reconstruction.

The described techniques are also applicable to imaging modalities other than x-ray CT. Thus, for example, the techniques may be applied in coherent scatter CT, positron emission tomography (PET), single photon emission computed tomography (SPECT), or other applications in which motion compensation is required.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

Having thus described the preferred embodiments, the invention is now claimed to be:

1. A computed tomography apparatus comprising:
   a motion calculator;
   a reconstructor which reconstructs energy resolved first radiation projection data to generate first image data indicative of an object under examination at least first and second motion states, wherein the motion calculator uses the first image data to calculate a motion of the object, and wherein the reconstructor further performs a motion compensated reconstruction using the calculated motion and second radiation projection data to generate second image data indicative of the object.

2. The apparatus of claim 1 including an energy pre-processor which uses a pre-processing technique to generate the energy resolved projection data.

3. The apparatus of claim 2 wherein the pre-processing technique includes a k-edge detection technique.

4. The apparatus of claim 2 wherein the energy pre-processor receives input signals indicative of radiation detected in at least three energy bins.

5. The apparatus of claim 1 wherein the second radiation projection data includes at least one of Compton effect data and photo-effect data.

6. The apparatus of claim 1 wherein the first energy resolved projection data includes projection data which has been pre-processed to selectively identify a substance present in the object.

7. The apparatus of claim 6 wherein the substance includes a contrast agent.

8. The apparatus of claim 6 wherein the substance includes bone or soft tissue.

9. The apparatus of claim 6 wherein the substance includes calcium or water.

10. The apparatus of claim 1 wherein the object includes a beating heart, the first and second motion states include first and second cardiac phases, and the first image data includes first data representative of the first cardiac phase and second data representative of the second cardiac phase.

11. The apparatus of claim 1 wherein the motion calculator calculates a plurality of three dimensional motion vectors.

12. The apparatus of claim 1 including
an object support which supports the object in an examination region;
an x-ray source which emits radiation at each of a plurality of angular positions with respect to the examination region;
an energy resolving x-ray detector which detects x-radiation emitted by the source and which has traversed the examination region.

13. A tomographic method comprising:
reconstructing energy resolved first projection data to generate first image data indicative of an object at least first and second motion states;
using the first image data to estimate a motion of the object;
reconstructing second projection data to generate second image data indicative of the object, wherein reconstructing the second projection data includes using the estimated motion to compensate for a motion of the object during acquisition of the second projection data.

14. The method of claim 13 including performing, prior to the step of reconstructing the energy resolved first projection data, an energy pre-processing of projection data acquired during a computed tomography scan of the object.

15. The method of claim 14 wherein the energy pre-processing includes processing projection data acquired during the scan to obtain projection data indicative of a substance of interest in the subject.

16. The method of claim 15 wherein the substance of interest includes a contrast agent.

17. The method of claim 14 wherein the energy pre-processing includes a k-edge detection.

18. The method of claim 13 including conducting a tomographic examination of an object using a tomographic examination apparatus which generates outputs indicative of detected ionizing radiation falling within at least two energy bins.

19. The method of claim 13 wherein the apparatus includes an energy resolving detector.

20. A computer readable storage medium containing instructions which, when executed by a computer, cause the computer to carry out a method which includes:
performing an energy processing operation to identify a substance of interest in an object;
estimating a motion of the identified substance;
using the estimated motion to perform a motion compensated reconstruction of tomographic projection data indicative of the object.

21. The computer readable storage medium of claim 20 wherein the substance of interest is a contrast agent.

22. The computer readable storage medium of claim 20 wherein the object includes a beating heart.

23. The computer readable storage medium of claim 20 wherein the energy processing operating includes k-edge imaging.

24. The computer readable storage medium of claim 20 wherein estimating a motion includes using image data indicative of first and second motion states to generate a motion vector.

25. The computer readable storage medium of claim 24 wherein the motion compensated reconstruction includes a backprojection and the method includes using the motion vector to modify a voxel position according to a motion state of a projection to be backprojected.

26. The computer readable storage medium of claim 20 wherein the energy processing operation includes an energy pre-processing operation.

* * * * *